(12) United States Patent
Cannon-Carlson et al.

(10) Patent No.: US 7,393,631 B2
(45) Date of Patent: Jul. 1, 2008

(54) METHOD FOR PURIFYING ADENOVIRUSES

(75) Inventors: Susan V. Cannon-Carlson, Wayne, NJ (US); Collette Cutler, Bloomingdale, NJ (US); Gary J. Vellekamp, Glen Ridge, NJ (US); Marcio Voloch, New York, NY (US)

(73) Assignee: Schering Corporation, Kenilworth, NJ (US)

( * ) Notice: Subject to any disclaimer, the term of this patent is extended or adjusted under 35 U.S.C. 154(b) by 4 days.

(21) Appl. No.: 11/326,275

(22) Filed: Jan. 5, 2006

(65) Prior Publication Data

US 2006/0105456 A1    May 18, 2006

Related U.S. Application Data

(63) Continuation of application No. 09/991,080, filed on Nov. 16, 2001, now abandoned.

(60) Provisional application No. 60/253,823, filed on Nov. 29, 2000.

(51) Int. Cl.
    *C12Q 1/70* (2006.01)
(52) U.S. Cl. .......................................................... 435/5
(58) Field of Classification Search .............. 424/233.1; 435/5
    See application file for complete search history.

(56) References Cited

U.S. PATENT DOCUMENTS

| 5,141,863 | A | 8/1992 | Suzuki et al. |
| 5,496,926 | A | 3/1996 | Rubinstein et al. |
| 5,723,438 | A | 3/1998 | Rubinstein et al. |
| 5,837,520 | A | 11/1998 | Shabram et al. |
| 6,261,823 | B1 | 7/2001 | Tang et al. |
| 6,365,713 | B1 | 4/2002 | Rubinstein et al. |
| 6,689,600 | B1 | 2/2004 | Wu et al. |
| 6,726,907 | B1 | 4/2004 | Zhang et al. |
| 7,125,706 | B2 | 10/2006 | Zhang et al. |
| 7,235,391 | B2 | 6/2007 | Wu et al. |
| 2002/0004226 | A1 | 1/2002 | Rubinstein et al. |

FOREIGN PATENT DOCUMENTS

| GB | 2 348 886 A | | 10/2000 |
| JP | 7-173189 | | 7/1995 |
| JP | 8-188599 | | 7/1996 |
| JP | 9-169794 | | 6/1997 |
| WO | WO 96/27677 | * | 9/1996 |
| WO | WO 97/08298 | * | 3/1997 |
| WO | WO 99/41416 | | 8/1999 |

OTHER PUBLICATIONS

Boulanger et al., *Eur. J. Biochem*, 39:37-42 (1973).
Smith, R. G. and S. A. Lee, "Large Scale Isolation and Partial Purification of type C RNA Viruses on Hydroxyapatite", *Analytical Biochemistry*, 86:252-263 (1978).
Tsuru, S. et al., "Adsorbtion and Preparation of Human Viruses Using Hydroxyapatite Column", *Bio-Medical Materials and Engineering*, 1: 1-5 (1991).
Yu, Z. et al., "Chromatographic Characteristics of Crude Preparations of rous Sarcoma Virus Strains on Hydroxylapatite", *Acta Virology*, 12:286 (1968).
International Search Report for International Application No. PCT/US01/44684.

* cited by examiner

*Primary Examiner*—Jeffrey S. Parkin
(74) *Attorney, Agent, or Firm*—Carol M. Gruppi

(57) ABSTRACT

Methods for purifying adenoviruses from a contaminated sample using a hydroxyapatite medium are provided. Sodium chloride concentrations present in buffers used throughout the method are at least 150 mM to prevent the adenovirus from irreversibly binding to the hydroxyapatite. Levels of contaminants and empty adenovirus capsids from samples purified by conventional purification techniques are further reduced to provide a highly pure adenovirus preparation.

19 Claims, No Drawings

METHOD FOR PURIFYING ADENOVIRUSES

CROSS-REFERENCE TO RELATED APPLICATION

This application is a continuation of U.S. Ser. No. 09/991,080 filed on Nov. 16, 2001 now abandoned, which claims benefit of priority from U.S. Provisional Patent Application Ser. No. 60/253,823, filed Nov. 29, 2000, the disclosures of which are hereby incorporated by reference in their entirety.

FIELD OF INVENTION

This invention relates to methods for purifying adenoviruses from a contaminated sample using a hydroxyapatite chromatographic medium.

BACKGROUND OF THE INVENTION

Adenoviruses are preferred in many gene therapy applications as a vector to deliver the therapeutic gene. The cultivation and purification of adenoviruses containing therapeutic genes, such as tumor suppressor genes and other biological response modifiers, have become increasingly important for gene therapy and vaccine development. As studies of gene therapy progress to clinical trials, larger quantities of purified viral vectors are needed to deliver the therapeutic gene in treatment. The relatively large diameter (approximately 80 nm) and fragile structure of adenoviruses make their purification challenging using conventional methods, e.g., cesium chloride density centrifugation and gel filtration chromatography, which have scale limitations. Chromatographic protocols for purifying live adenoviruses are known, e.g., see U.S. Pat. No. 5,837,520, however, small amounts of contaminating proteins and incomplete virus particles, e.g., empty capsids, are found in virus preparations using these protocols. This is a significant problem since empty capsids and other protein contaminants can be immunogenic in vivo. Therefore, it would be advantageous to have an effective process that provides a sample of highly purified viable virus, while significantly reducing levels of incomplete virus particles. Improved virus purity without sacrifice to virus yield would be beneficial in large-scale adenovirus production.

Thus, there is a need in the art for improved purification methods for adenoviruses that can resolve live virus from incomplete viral particles and other contaminating proteins in the viral preparation. The present invention addresses this and other needs in the art.

SUMMARY OF THE INVENTION

This invention provides a method for purifying biologically active adenoviruses from a contaminated sample using a hydroxyapatite medium under conditions which permit the adenovirus to reversibly bind to the hydroxyapatite while contaminants are passed. The present purification method greatly reduces the level of contaminants and empty adenovirus capsids from adenovirus samples first purified by conventional purification methods. The concentration of sodium chloride present in buffers used throughout the method is at least 150 mM to prevent the adenovirus from irreversibly binding to the hydroxyapatite. Lower sodium chloride concentrations can cause adenovirus to irreversibly bind to the hydroxyapatite.

It is an advantage of a method of the invention that empty capsids, i.e., incomplete viral particles, which are not infectious and thus not useful for gene therapy or other applications, are separated from intact viruses. Thus, a highly purified and resolved, infectious adenovirus sample is provided.

Thus, a method for purifying biologically active adenovirus from a contaminated sample pool is provided, which includes the steps of contacting the sample pool with a hydroxyapatite chromatographic medium to reversibly bind the biologically active adenovirus to the hydroxyapatite, followed by eluting the bound biologically active adenovirus from the hydroxyapatite.

In a specific embodiment, the sample pool used in a method of the invention contains a buffered solution including about 50 mM sodium phosphate pH about 7.5, about 400 mM sodium chloride, about 2% sucrose, about 2 mM $MgCl_2$, and about 10% glycerol.

DETAILED DESCRIPTION OF THE INVENTION

In accordance with the present invention, there may be employed molecular biology, microbiology, or recombinant DNA techniques within the ordinary skill of the art to prepare, grow and cultivate viruses used in a method of the invention. Such techniques are explained fully in the literature. See, e.g., Sambrook, Fritsch & Maniatis, Molecular Cloning: A Laboratory Manual, Second Edition (1989), Cold Spring Harbor Laboratory Press, Cold Spring Harbor, N.Y.; DNA Cloning: A Practical Approach, Volumes I and II (D. N. Glover ed. 1985); Oligonucleotide Synthesis [M. J. Gait ed. (1984)]; Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; A Practical Guide To Molecular Cloning [B. Perbal (1984)]; Current Protocols in Molecular Biology, John Wiley & Sons, Inc., F. M. Ausubel et al., eds., 1994; Virology: A laboratory manual. Academic Press, New York, (Burleson, ed., 1992).

This invention provides a method for purifying biologically active adenoviruses from incomplete virions and various viral and non-viral protein contaminants in a sample using a hydroxyapatite medium.

The term "contaminant" means an undesirable impurity in a sample containing adenovirus, e.g., an empty capsid (which is an immature viral particle lacking viral DNA and containing precursors to mature viral proteins such as pVIII, and is not capable of adhering to or penetrating a suitable cell), a nucleic acid molecule, a free viral protein (e.g., viral proteins III or hexon), a non-viral protein (e.g., host or media derived proteins such as BSA, which is a common cell culture component in mammalian systems). An advantage of the present purification method is that the hydroxyapatite medium used under salt and buffer conditions in accordance with the invention reduces the level of incomplete virus particles in the adenovirus sample.

The term "purifying", and grammatical variations thereof, when used in reference to a method of the present invention, means at least a 50% reduction of total contaminants, in particular, free viral and non-viral proteins, in an adenovirus sample, as quantitated by silver stain SDS gel chromatography, over an adenovirus sample that is purified using a conventional purification method (i.e., a purification method known in the art other than the use of hydroxyapatite, e.g., DEAE chromatography) before a purification step of the present invention. Preferably the reduction in total contaminants is at least 80%. Most preferably the reduction in total contaminants is 90% or better. The reduction in empty capsids is at least 50%, preferably 75%, more preferably 80%, and most preferably 85% or better, as quantitated using reverse phase HPLC by measuring a viral protein precursor to adenovirus protein VIII ("pVIII") [see Galibert et al., Gene 6: 1 (1979) and Herisse et al., Nucl. Acids Res. 8: 2173 (1980)], which is not found in mature, infectious adenoviruses. It is noted that a method of the present invention that is scaled up for commercial production may result in slightly lower percent reductions, preferably not more than 5 to 10% lower reductions.

Any adenovirus can be purified by the present invention, whether it is a wild type, mutant, or recombinant. Type 2 and type 5 adenoviral vectors are preferred. Adenoviruses can be prepared and cultivated according to methods known in the art, e.g., see Wills et al., Hum. Gene Ther. 5: 1079-1088 (1994), Hughye et al., Hum. Gene Ther. 6: 1403-1416 (1995), and laboratory manuals as described, supra.

Adenoviruses purified by the present method are "infectious", which means they comprise a multi-subunit capsid that encapsulates a nucleic acid molecule and can interact with a receptor on a suitable cell to result in a transfer of the nucleic acid from the adenovirus into the cell.

An "empty capsid" is an incomplete virus particle that is not infectious, e.g., a virus particle that has a capsid, but lacks a nucleic acid molecule.

An adenovirus used in this invention is preferably replication deficient such that the virus cannot reproduce after it infects a cell. These viruses are well-known in the art.

An adenovirus can include a heterologous nucleic acid sequence e.g., a therapeutic gene, that can be transferred from the viral vector to a host cell for use in gene therapy. A "therapeutic gene" is a DNA sequence that encodes a particular sequence of amino acids which comprise all or part of one or more proteins and that has a desired therapeutic effect. The therapeutic gene may or may not include regulatory DNA sequences, such as promoter sequences, which determine, for example, the conditions under which the gene is expressed. Preferably, a therapeutic gene replaces an absent or mutated gene that causes an increase in pathological cell growth or proliferation of cells. Once in a host cell, a therapeutic gene can exhibit a corresponding therapeutic effect by, e.g., remaining extrachromosomal such that the gene is expressed by the cell from the extrachromosomal location, or incorporating into the host cell genome in a recombination event with the endogenous gene. Methods for introducing heterologous nucleic acid sequences into a viral vector are well known in the art.

Examples of therapeutic genes include tumor-suppressor genes, e.g., Rb and mutants thereof, p53 and mutants thereof, p21 and mutants thereof, DCC, NF-1, Wilm's tumor, NM 23, BRCA-1, BRCA-2, BRUSH-1, p56, H-NUC, thyroid hormone receptor gene, retenoic acid receptor gene, genes encoding p130, p107, and p85. Other gene replacement or supplementation strategies include adenosine deaminase (ADA), thymidine kinase (TK), genes encoding various cytokines, e.g., γ-interferon, α-interferon, IL-2, IL-10 and hormones. A therapeutic gene also includes DNA encoding a ribozyme, i.e., a DNA construct that encodes an RNA enzyme which binds and destroys the RNA of selected positively-acting growth regulatory genes, such as oncogenes or proto-oncogenes including, but not limited to: c-myc, c-fos, c-jun, c-myb, c-ras, KC and JE; and growth factor receptor genes including but not limited to: epidermal growth factor, platelet derived growth factor, transferrin and insulin. Most preferably the therapeutic gene is a tumor suppressor gene, e.g., Rb, p53, BRUSH-1, p56, BRCA-1, BRCA-2, p16 or p21, or a mutant gene thereof. In a specific embodiment, the adenoviral vector harbors the p53 gene (e.g., the adenoviral vector is ACN53).

Surprisingly, it has been discovered that adenovirus is efficiently purified from empty capsids and contaminants using a hydroxyapatite medium provided the minimum concentration of sodium chloride is at least 150 mM in buffered solutions used throughout the method. The minimum sodium chloride concentration prevents the virus from irreversibly binding to the hydroxyapatite medium. More preferably, buffered solutions used in this invention contain from about 350 to 450 mM sodium chloride. It is noted that concentrations of 500 mM or greater sodium chloride can cause the virus to become unstable, and preferably are not used in a method of the invention. One skilled in the art can substitute other salts for sodium chloride, if desired, at suitable concentrations (having similar conductivity), including monovalent ionic and cationic salts, e.g., KCl or $NH_4Cl$, or divalent anionic and cationic salts, e.g., $Na_2SO_4$ or $(NH_4)_2SO_4$.

A "buffered solution" is an aqueous solution which contains sodium chloride and a suitable buffer to maintain the pH of the solution between about 6.8 to 9.0, preferably between about pH 7.0 to 8.0, most preferably between about pH 7.4 to 7.6. In a specific embodiment of the invention, the pH is 7.5. Buffers having a pKa within the desired pH range are preferred. A buffered solution does not cause an adenovirus to irreversibly bind to a hydroxyapatite medium. Buffered solutions are used, e.g., in a sample pool containing the adenovirus, to equilibrate and wash (equilibration and wash buffers) the hydroxyapatite medium, and to elute (elution buffers) the adenovirus bound to the hydroxyapatite.

Examples of buffers that can be used in the invention include phosphate, MES, HEPES, MOPS, Borate, TRIS, BES, ADA, ACES, PIPES, MOPSO, BIS-TRIS PROPANE, BES, TES, DIPSO, TAPSO, TRIZMA, HEPPSO, POPSO, TEA, EPPS, TRICINE, GLYCYLGLYCINE, BICINE, TAPS, and the like. Phosphate buffer in a concentration of about 25 to 100 mM, more preferably about 50 mM is preferred.

Buffered solutions used in this invention can also be formulated with a stabilizing or tonicity-adjusting agent, e.g., polyhydroxy hydrocarbons such as glycerol, disacharrides such as sucrose, divalent metal salt stabilizers such as magnesium, zinc and calcium salt, and monovalent metal salt stabilizers such as potassium, sodium, lithium and cesium salts. These additional agents are particularly useful when the sodium chloride concentration in the sample pool is greater than 350 mM.

Formulations of aqueous buffered solutions that can be used in a method of this invention are described in International Patent Publication No. WO 99/41416, which is incorporated herein by reference in its entirety. For example, depending on the virus concentration, a buffer used in the invention can contain less than 1% glycerol to about 20% glycerol and/or less than 1% to about 5% sucrose. At $1 \times 10^{14}$ or less virus particles per ml, the concentrations of glycerol and sucrose can be about 5 to 10% and about 0.5 to 2% respectively.

A "sample pool" is a buffered solution that contains adenovirus and a contaminant, which may have been prepared from a conventional purification method, from which the further purification of the adenovirus is desired. Preferably, a sample pool is formulated with additional stabilizing or tonicity-adjusting agents, as described above. In one embodiment a sample pool contains about 50 mM $NaPO_4$ (pH 7.5), 400 mM NaCl and 10% glycerol.

A sample pool typically contains a concentration range of adenovirus from about $1 \times 10^9$ to about $1 \times 10^{14}$ per ml. Preferably, the sample pool is formulated with one or more stabilizing agents, such as glycerol and sucrose, as described above, particularly when higher concentrations of virus are used.

A sample pool can be prepared from a cell lysate. For example, cells such as 293 cells, infected with adenovirus are removed from the growth environment and their cell membranes disrupted, e.g., by physiological or chemical means, according to methods well known in the art (see Wills et al., supra and Hughye et al., supra). The cell lysate containing the adenovirus is preferably first subjected to one or more conventional chromatography methods to provide a virus sample pool, which is further purified according to a method of the invention. For example, a cell lysate containing adenovirus can be processed to enzymatically degrade DNA and RNA followed by a conventional purification method, including anion-exchange chromatography, gel filtration (size-exclusion) chromatography, hydrophobic interaction chromatography or immobilized metal affinity chromatograpy. Combinations of these methods can be used if desired, e.g., see U.S. Pat. No. 5,837,520, which is incorporated herein by reference in its entirety. Preferably, the conventional method used is an anion-exchange chromatography.

The conventional chromatography methods remove most of the cellular debris and some of the unassembled viral proteins and non-viral protein contaminants, however, a variety of contaminants, e.g., BSA, viral proteins such as free hexon, and incomplete virions lacking viral DNA (empty capsids), may remain in the samples. Surprisingly, these contaminants are efficiently removed by a purification method using hydroxyapatite, which improves the purity, resolution and quality of adenovirus in the sample compared with the conventional viral purification methods.

The hydroxyapatite medium used in a method of the invention can be prepared as a chromatographic column according to conventional methods well known in the art. For example, an HA column can be prepared for traditional (gravity) column chromatography, fast performance chromatography or high pressure liquid chromatography using radial or axial flow fluidized bed columns, as desired.

The hydroxyapatite medium is preferably washed and equilibrated using a buffered aqueous solution, as described supra, before purifying the adenovirus according to this invention. In a specific embodiment, an equilibration buffer used to equilibrate the hydroxyapatite contains about 50 mM $NaPO_4$ (pH 7.5), 400 mM NaCl, 2% sucrose, 10% glycerol and 2 mM $MgCl_2$. The column can be equilibrated until the eluent reaches the pH and conductivity of the buffer, typically about five to ten bed volumes.

After the hydroxyapatite is washed, the sample pool is contacted with the hydroxyapatite media to permit the adenovirus to reversibly bind to the hydroxyapatite and the contaminants to pass through the media, thus separating the contaminants from the virus.

The hydroxyapatite column, which contains the bound adenovirus, is washed with a wash buffer, which can be the same buffer used to equilibrate (equilibration buffer) the hydroxyapatite. After washing the adenovirus-bound hydroxyapatite column, the adenovirus can be eluted from the hydroxyapatite using a gradient elution or step elution to phosphate in equilibration buffer (elution buffer). If gradient elution is desired, the adenovirus can be eluted using, e.g., about a 5 to 30 bed volume gradient to, e.g., 200 mM sodium phosphate in equilibration buffer. Preferably, a 10 bed volume gradient is used. If step elution is desired, the elution buffer can be equilibration buffer containing preferably about 150 to 250 mM phosphate.

The present method is performed in a temperature range from about 5 to 30° C., more preferably from about 15 to 27° C. Most preferably the method is performed at room temperature, e.g., about 20 to 27° C. It is noted that at less than about 15° C., the virus may begin to irreversibly bind to the column depending on the salt conditions and presence of stabilizing agents. One having ordinary skill in the art can optimize conditions in accordance with the invention as desired.

The non-viral proteins and high molecular weight contaminants elute in the spent charge and wash of the column. The empty capsids bind more tightly to hydroxyapatite than the biologically active virus, and thus empty capsids do not elute from the hydroxyapatite with the biologically active virus. The fractions off the column can be analyzed by UV absorbance, Resource Q analytical HPLC and rp-HPLC, and used to make a single pool of purified biologically active adenovirus.

EXAMPLE

This Example demonstrates a purification method of the present invention using hydroxyapatite in comparison with a conventional virus purification method.

Adenoviruses containing the p53 gene (ACN53), cultivated from mammalian 293 cells, were captured from cell lysates using a conventional DEAE anion-exchange chromatography method. The sample pool from the DEAE contained a 31 kDa protein (pVIII), which corresponds to a precursor of adenoviral protein VIII (hexon associated protein).

The DEAE pool was prepared as a sample pool for use in a purification method of the invention by buffering to 50 mM $NaPO_4$ (pH 7.5), 400 mM NaCl, and 5 to 10% glycerol. Hydroxyapatite columns (0.5×10 cm, 0.5×20 cm, and 1.6×15 cm), equilibrated into 50 mM $NaPO_4$ (pH 7.5), 400 mM NaCl, 2% sucrose and 2 mM $MgCl_2$, were prepared by packing. The buffered DEAE pool was applied to the hydroxyapatite column, washed with equilibration buffer as described, and the adenovirus eluted using a gradient elution to 600 mM phosphate in equilibration buffer or by step elution with 250 mM phosphate in equilibration buffer.

Reverse-phase HPLC and size-exclusion HPLC showed that in the hydroxyapatite eluate compared with the DEAE pool there was a significant reduction in incomplete virus particles and free viral proteins, e.g., at least 75% reductions in pVIII, reduction of free penton to undetectable levels and 40% reduction in free hexon.

Densitometric analyses of silver stained SDS-PAGE demonstrated that hydroxyapatite also efficiently removed total non-viral protein contaminants, i.e., an 80 to 90% reduction of proteins which are resolved from intact virions in CsCl gradients (e.g., 70 to 85% reductions in BSA), and high molecular weight complex proteins, i.e., a 25% reduction of unidentified proteins cosedimenting with the virus in CsCl gradients. In experiments where BSA was spiked into the feed to the column, the BSA passed through the column without binding to the hydroxyapatite under the buffer conditions described, demonstrating that the hydroxyapatite chromatography efficiently resolves BSA from the sample.

Polymerase chain reaction analyses of nucleic acids present in the eluate showed an 8-fold reduction in short fragments and a 100-fold reduction in medium fragments.

Thus, use of hydroxyapatite chromatography under the buffer and salt conditions described to purify adenovirus samples provides an adenovirus sample having great resolution for use in gene therapy or other virus applications requiring high purity.

The present invention has been described herein with reference to certain preferred embodiments and an example. Since obvious variations will appear to those skilled in the art, the invention is not to be considered limited thereto, but only by the claims which follow.

What is claimed is:

1. A method for purifying adenovirus from contaminants in a sample pool, comprising: contacting the sample pool with a hydroxyapatite chromatographic medium to reversibly bind the adenovirus to the hydroxyapatite; and eluting the bound adenovirus from the hydroxyapatite, wherein the sample pool comprises at least 150 mM concentration of sodium chloride and the elution buffer comprise at least 150 mM concentration of sodium chloride.

2. The method of claim 1 wherein the sample pool comprises sodium chloride in a concentration of from about 150 to 500 mM.

3. The method of claim 1, wherein the hydroxyapatite chromatographic medium is equilibrated with a buffer comprising sodium chloride at a concentration of from about 150 to 500 mM before the step of contacting the sample pool with the hydroxyapatite.

4. The method of claim 1, further comprising the step of washing the hydroxyapatite with a buffer comprising sodium chloride in a concentration of 150 to 500 mM, wherein the hydroxyapatite comprises an adenovirus bound thereto.

5. The method of claim 1, wherein the adenovirus is eluted using a buffer comprising sodium chloride in a concentration from about 150 mM to 500 mM.

6. The method of claim 1 wherein the sodium chloride concentration in a buffer used in the method is from about 350 mM to 450 mM.

7. The method of claim 1, wherein the sample pool is prepared from an eluate of a conventional chromatography medium.

8. The method of claim 7 wherein the conventional chromatography medium is: an anion exchange resin; an immobilized metal ion affinity resin; a size exclusion chromatography resin; or a medium used in hydrophobic interaction chromatography.

9. The method of claim 1, wherein the eluting step is a gradient elution to 600 mM phosphate.

10. The method of claim 1, wherein the eluting step is a step elution with 250 mM phosphate.

11. The method of claim 1, wherein a buffer used in the method comprises glycerol or sucrose.

12. The method of claim 1, wherein the concentration of adenovirus in the sample pool is equal to or less than $1 \times 10^{14}$ particles per ml.

13. The method of claim 1, wherein the adenovirus comprises a therapeutic gene.

14. The method of claim 1, wherein the adenovirus is ACN53.

15. The method of claim 1, wherein the adenovirus comprises a nucleic acid sequence from the p53 gene or from the p21 gene.

16. A method of claim 1, which reduces the concentration of a contaminant in the sample pool by at least 80%.

17. A method of claim 1, which reduces the concentration of empty capsids by at least 75%.

18. A method of claim 1, which reduces the concentration of BSA by at least 70%.

19. A method for purifying adenovirus from contaminants in sample pool, comprising: contacting the sample pool with a hydroxyapatite chromatographic medium to reversibly bind the adenovirus to the hydroxyapatite; washing the adenovirus-bound hydroxyapatite with a buffered solution; and eluting the bound adenovirus from the hydroxyapatite, wherein the sample pool is a buffered solution comprising about 50 mM sodium phosphate pH about 7.5, about 400 mM sodium chloride, about 2% sucrose, about 2 mM $MgCl_2$, and about 10% glycerol, and the concentration of total contaminants is reduced by at least 80%.

* * * * *